United States Patent [19]
Shortle et al.

[11] Patent Number: 5,869,644
[45] Date of Patent: Feb. 9, 1999

[54] SYNTHESIS OF DIVERSE AND USEFUL COLLECTIONS OF OLIGONUCLEOTIDIES

[75] Inventors: David R. Shortle, Baltimore, Md.; John Sondek, New Haven, Conn.

[73] Assignee: The Johns Hopkins University, Baltimore, Md.

[21] Appl. No.: 689,346

[22] Filed: Aug. 8, 1996

Related U.S. Application Data

[63] Continuation of Ser. No. 66,178, filed as PCT/US93/03418, Apr. 13, 1993, abandoned, which is a continuation-in-part of Ser. No. 868,489, Apr. 15, 1992, abandoned.

[51] Int. Cl.$^6$ .......................... C07H 21/00; C12N 15/00
[52] U.S. Cl. ...................... 536/25.3; 435/172.3; 435/91.1
[58] Field of Search ................................ 435/91.1, 69.1, 435/172.3; 536/25.3

[56] References Cited

U.S. PATENT DOCUMENTS 5,264,563  11/1993  Huse ........................................ 536/25.3

FOREIGN PATENT DOCUMENTS

| 0 247 647 | 1/1991 | European Pat. Off. . |
| 0 590 689 A2 | 4/1994 | European Pat. Off. . |
| 91/19818 | 12/1991 | WIPO . |

OTHER PUBLICATIONS

Sonveaux, "The organic chemistry underlying DNA synthesis", Bioorg. Chem. 14: 274–325, 1986.
Bannwarth et al., "Laboratory Methods: A System for the Simultaneous Chemical Synthesis of Different DNA Fragments on Solid Support", *DNA* 5(5):413–419 (1986).
Ner et al., "Laboratory Methods: A Simple and Efficient Procedure for Generating Random Point Mutations and for Codon Replacements Using Mixed Oligodeoxynucleotides" *DNA* 7(2):127–134 (1988).
Ner et al., "A Method for Introducing Random Single Point Deletions in Specific DNA Target Sequences Using Oligonucleotides" *Nucleic Acid Research* 17(11):4015–4023 (1989).
Crea, et al., 1978, Chemical synthesis of genes for human insulin, *Proc. Natl. Acad. Sci. USA*, 75:5765–5769.
Crea, et al., 1980, "Synthesis of oligonucleotides on cellulose by a phosphotriester method," *Nucleic Acids Research*, 8:2331–2348.
Hui, et al., 1984, "Mutagenesis of the three bases preceding the start codon of the β–galactosidase mRNA and its effect on translation in *Escherichia coli*," *The EMBO Journal*, 3:623–629.
Sirotkin, K., 1986, Advantages to Mutagenesis Techniques Generating Populations Containing the Complete Spectrum of Single Codon Changes, *J. Theor. Biol*, 123:261–279.
Virnekäs, et al., 1994, Trinucleotide phosphoramidites: ideal reagents for the synthesis of mixed oligonucleotides for random mutagenesis, *Nucleic Acids Research*, 22:5600–5607.
Wells et al. (1985) Cassette mutagenesis: an efficient method for generation of multiple mutations at defined sites. Gene 34: 315–323.
Zon et al. (1985) Analytical studies of mixed sequence' oligodeoxyribo nucleotides synthesized . . . Nucleic Acids Res. 13: 8181–8196.
Beaucage et al. (1992) Advances in the synthesis of oligonucleotides by The phosphoramidate approach. Tetrahedron 46: 2223–2311.
Ike et al. (1983) Solid phase synthesis of polynucleotides, VIII. Synthesis of mixed oligonucleotides by the phosphotriester . . . Nucleic Acids Res. 11:477–488.

*Primary Examiner*—Jasemine C. Chambers
*Assistant Examiner*—Scott D. Priebe
*Attorney, Agent, or Firm*—Banner & Witcoff, Ltd.

[57] ABSTRACT

A new technique for generating mixtures of oligonucleotides in a single automated synthesis is taught. The method can be used to prepare mixed oligonucleotides ideally suited for creation of useful mixtures of oligo- or polypeptides or proteins. Additionally, the technique enables insertion and/or substitution and/or deletion of a nucleotide sequence at one or more sites. For protein mutagenesis, a trinucleotide can be inserted or substituted at codon boundaries. The invented technique makes possible the encoding of all possible single amino acid insertions, or any desired mixture of substitutions and insertions.

17 Claims, 4 Drawing Sheets

SYNTHESIS OF DIVERSE AND USEFUL COLLECTIONS OF OLIGONUCLEOTIDIES

This application is a continuation of application Ser. No. 08/066,178, filed Sep. 30, 1994, now abandoned, which is a 371 of PCT/US93/03418 filed Apr. 13, 1993 and which is a continuation-in part of application Ser. No. 07/868,489, filed Apr. 15, 1992.

FIELD OF THE INVENTION

The present invention relates to the synthesis of oligonucleotides, and specifically a new method for generating mixtures of oligonucleotides in a single automated synthesis. The technique enables the generation of diverse mixtures of DNA which can be used to prepare large collections of oligo- or polypeptides and/or proteins:

BACKGROUND OF THE INVENTION

Methods of preparing DNA of mixed composition are becoming increasingly important in the study of biomolecular function as well as in the search for substances with new and useful properties. As DNA synthesis technology improved in the early 1980's, it became feasible to perform multiple syntheses as a means of generating mixtures of oligonucleotides. In principle, large and diverse collections could be made in multiple syntheses. In practice, several investigators realized that large numbers of oligonucleotides could be generated in a single synthesis by coupling mixtures of mononucleotides, instead of unique monomer building blocks. The complexity of the resulting collection or "library" of oligonucleotides is determined by the number of monomers coupled, and the number of sites at which mixtures of monomers are introduced.

Oligonucleotides of mixed composition are increasingly being used in protein mutagenesis for the study of structure and function. By expressing DNA sequences of mixed composition, a corresponding library of mutant proteins is generated. Allied with appropriate screening techniques, such libraries can be searched for substances with altered properties, and are therefore useful in the study of biomolecular function. The most general class of mutagenesis methods employs oligonucleotides based on the sequence of the wild-type gene, and incorporating modifications that will eventually give rise to any desired amino acid sequence changes. These methods were recently reviewed in the August 1991 issue of Current Opinion in Structural Biology.

Virtually all genetic studies of protein structure and activity employ substitution mutations: one or several amino acid side chains are replaced, but the length of the protein and the spacing of residues are conserved. In order to facilitate the generation of large numbers of substitution mutations in a single experiment, a number of prior art techniques have been developed (for review, see Botstein, D. & Shortle, D. (1985) *Science* 229, 1193–1201 and Zoller, M. J. (1991) *Curr. Opin. Struct. Biol.* 1, 605–610), the most popular of which involve the chemical synthesis of complex mixtures of oligonucleotides which are used either as mutagenic primers for DNA synthesis (see Hermes, J. D., Parekh, S. M., Blacklow, S. C., Koster, H., & Knowles, J. R. (1989) *Gene* 84, 143–151) or as mutagenic duplex fragments for ligation to restriction fragments (see Matteucci, M. D. & Heynecker, H. L. (1983) *Nucl. Acids Res.* 11, 3113–3121). To generate the required single amino acid substitutions, each monomer used for oligonucleotide synthesis is "doped" with small amounts of the three non-wild type mononucleotides. In principle, this method can provide every possible nucleotide substitution in a gene segment in a single experiment. Since the distribution of nucleotide substitutions will follow Poisson statistics, two mononucleotide replacements in the same codon will be relatively rare at levels of doping that give one or just a few amino acid substitutions per mutant gene. Consequently, for practical purposes, this strategy for generating mixtures of mutagenic oligonucleotides can be expected to yield only one third of all possible amino acid substitutions, with the types of amino acid substitutions induced at a particular position being determined by the sequence of the wild-type codon. It should also be noted that prior art monomer doping of oligonucleotides cannot be used to induce other types of changes in DNA sequence, such as insertions or deletions.

A related application of mixed DNA synthesis uses vast collections of diverse oligonucleotides in processes directed at discovering substances with new and useful properties. Libraries of peptides (Cwirla, S. E., Peters, E. A., Barrett, R. W., & Dower, W. J. (1990) *Proc. Natl. Acad. Sci. USA* 87, 6378–6382), RNA (Tsai, D., Kenan, D., & Keene, J. (1992) *Proc. Natl. Acad. Sci., USA* 89, 8864–8868) and DNA (Bock, L., Griffin, L., Latham, J., Vermaas, E., & Toole, J. (1992) *Nature* 355, 564–566), all of which were generated from collections of oligonucleotides prepared by mixed monomer synthesis, have been screened to locate molecules which bind to particular target substances. In this approach, the utility of peptide libraries is critically dependent on the way in which the oligonucleotide mixture is generated. This arises because of the degeneracy of the genetic code: amino acids are not represented by equal numbers of trinucleotide codons, some amino acids being encoded by only one codon, some by as many as six. Therefore, although oligonucleotides prepared from equal mixtures of all four monomers may contain each of the 64 trinucleotides, the encoded amino acids are represented unevenly, and "stop" codons are unavoidably generated. As a result, amino acids which are encoded by the largest number of codons are overrepresented at the expense of those encoded by only one or two codons. By way of example, if a particular type of mutation is desired (for example substitution of only hydrophobic amino acids), the resulting library will contain a high proportion of undesired species. This drawback is particularly critical as the number of positions at which substitutions are made increases.

In an attempt to improve the efficiency of synthesizing mixed DNA sequences for preparation of peptide and protein libraries, schemes have been introduced in which monomers are mixed in a rational manner. For example, Youvan has calculated optimal mixtures of monomers for specifying particular subsets of amino acids (Arkin, A. P., & Youvan, D. C. (1992) *Bio/Technology*, 10, 297–300). Use of these mixtures increases the proportion of desired amino acids in a peptide or protein library. It does not, however, preclude generating undesired substitutions arising from particular combinations of monomers. Even with this method, the desired substitutions are usually a fraction of those introduced at each site. Consequently, as the number of sites altered increases, the proportion of desired mutants in the library decreases.

In recognition of the problems associated with the use of mixtures of monomers, Huse has described a method (disclosed in WO 92103461) in which DNA synthesis is performed so as to emulate multiple syntheses. This is achieved by carrying out the synthesis on multiple solid supports which can be mixed and re-divided when necessary. In this way, diverse mixtures of oligonucleotides can be made using monomers, and the problems associated with the degeneracy of the genetic code avoided. The method has two disadvantages: (i) for each synthesis, labour intensive dividing and re-mixing of support material is required, and (ii) the total number of different sequences which can be synthesized is limited by the number of physically separable supports used in the synthesis, which is typically of the order of 108.

In summary, existing methods of synthesis of multiple DNA sequences suffer several disadvantages:

1. Although every possible nucleotide substitution can be generated using oligonucleotides doped with mixed monomers, contiguous two and three mononucleotide substitutions are extremely uncommon. This is disadvantageous with regard to protein mutagenesis since each amino acid in a protein is specified by three contiguous nucleotides, and this strategy can efficiently generate only approximately one third of all possible amino acid substitutions for each wild-type amino acid in a single synthesis.

2. No strategy involving the synthesis of mixtures of oligonucleotides, as taught by the prior art, allows for the generation of mutant proteins with insertions of one or more codons at more than a single site in the synthesized oligonucleotide.

3. The degeneracy of the genetic code means that any mixture of mononucleotides used in mixed DNA synthesis unavoidably gives oligonucleotides containing undesired codons or does not provide all desired codons. This problem becomes critical as the number of positions at which mixtures are introduced increases.

4. Methods which simulate multiple syntheses are labour intensive, and the diversity of sequences which can be generated is limited by the number of physically separable supports used.

The present invention provides solutions to these problems and enables the preparation of mixed oligonucleotides with a multitude of applications in modern molecular biology. For example, mixed oligonucleotides prepared according to the present invention can be used to generate genes encoding peptide and/or protein libraries. Additionally, trinucleotides are useful in preparing degenerate primers for the polymerase chain reaction. The invention is particularly useful for protein mutagenesis; single-stranded mutagenesis primers and double-stranded "cassettes" encoding any combination of amino acids can be readily prepared by applying the method disclosed herein. The present invention also enables substitution, insertion, and deletion mutagenesis.

The method relies on the use of pre-synthesized oligonucleotides and additionally, specially protected mono- and oligonucleotides, which are compatible with the most efficient methods of DNA synthesis. Trinucleotide building blocks have been used previously in DNA synthesis (see, for example, Hirose, T., Crea, R., & Itakura, K. (1978) Tet. Lett., 2449–2452; Miyoshi, K., Miyake, T., Hozumi, T., & Itakura, K. (1980) Nucl. Acids Res., 8, 5473–5489) when stepwise coupling yields were low and it was more desirable to incorporate the largest possible oligonucleotide blocks at each step. This earlier work differs from the present invention as (i) it relied on inefficient and outdated phosphodiester chemistry and would therefore not allow multiple couplings, (ii) it was not directed at generating diverse and useful collections of mixed oligonucleotides, and (iii) it did not enable insertion and deletion mutagenesis.

SUMMARY OF THE INVENTION

The present invention overcomes the limitations in the prior art and provides a new technique for generating mixtures of oligonucleotides in a single automated synthesis. The method is useful in the systematic mutagenesis of proteins or other important genetic elements. The diverse oligonucleotide collections which can be generated by applying the present invention are particularly useful in the preparing peptide libraries which can be screened for molecules which bind to a particular target substance. The present invention can also be used in protein mutagenesis to encode all possible amino acid substitutions, all possible single amino acid insertions, all possible amino acid deletions or any desired mixture of substitutions and insertions.

In its most general form, the present invention allows for the synthesis of DNA molecules using oligonucleotide building blocks. Particularly preferred is the use of trinucleotides which correspond to amino acid codons. In the description that follows, trinucleotides are used to illustrate the method, although the use of oligonucleotides of different length is not precluded.

Trinucleotides are prepared so as to be compatible with standard methods of automated DNA synthesis. Most conveniently, the free 5' position is protected with an acid-labile protecting group (typically 4,4'-dimethoxytrityl, DMT), the phosphates are protected as methyl or cyanoethyl esters, the bases are protected as benzoyl (A and C) or isobutyryl (G) amides, and the free 3' position is activated for coupling as either an O-methyl or O-cyanoethyl N,N-diisopropylamino phosphoramidite. As described below, in some cases it is desirable that the 5' position is protected differently. This is readily achieved during trinucleotide synthesis. The method does not preclude the use of trinucleotides protected and activated in alternative ways.

The present invention can be used for either stoichiometric or sub-stoichiometric coupling of trinucleotides. In each case, the automated synthesizer proceeds step-wise to synthesize an oligonucleotide by coupling a sequence of monomers specifying the wild-type DNA sequence. At the desired site, the synthesis programme is suspended, and an altered sequence of steps is effected, as described below.

1. Stoichiometric Coupling

In a first embodiment, one or more trinucleotides are used in place of monomers for chemical DNA synthesis. The trinucleotides couple essentially quantitatively, and can therefore be used for automated DNA synthesis in the same way as monomer building blocks. In a single synthesis, stoichiometric coupling of trinucleotide mixtures provides DNA of any desired complexity with complete control over its composition. Stop codons can be avoided, and any combination of amino acids can be encoded at each position. Replacement of a wild-type codon with any combination of trinucleotides is readily performed by directing the DNA synthesizer to access an appropriate mixture at the desired step in the synthesis. The method is therefore ideal for the generation of peptide libraries of defined composition. It is also well-suited to preparing mutant oligopeptides or proteins in which a particular class of amino acids (e.g. hydrophobic) is introduced at one or more sites.

2. Sub-stoichiometric Coupling

By reducing the level of trinucleotide used during DNA synthesis, sub-stoichiometric coupling of suitably protected and activated trinucleotides can be used in order to achieve substitution, insertion or deletion mutagenesis. In this format, the present invention is well suited to generating mutant proteins bearing single amino acid substitutions for the study of structure-function relationships. One or more trinucleotides are added in an amount that is sub-stoichiometric to the number of 5' termini on the solid support. If a codon is to be inserted, the 5' end of the added trinucleotide is protected in the same way as the monomers used in the synthesis. If substitution or deletion is desired, the 5'-end of the trinucleotide bears a specially chosen stable protecting group, hereafter referred to as X. In this context, a stable protecting group X is any functionality capable of withstanding the conditions of automated DNA synthesis, but which can be selectively cleaved when necessary. The trinucleotide can be added at different points in the sequence of the wild-type gene. The end product is a complex mixture of oligonucleotides based upon the wild-type sequence but randomly doped with mixtures of unique or degenerate trinucleotides. Insertion, substitution, or deletion mutagenesis are achieved during sub-stoichiometric coupling as follows:

(i) Insertion (see FIG. 1)

In a second embodiment to generate insertion mutations, the trinucleotide is chosen to have one of the commonly used protecting groups at the 5' position, such as DMT. The small fraction of growing chains that undergo addition of the trinucleotide under sub-stoichiometric coupling conditions are deblocked immediately and then elongated in all subsequent steps. The net result is the addition of three nucleotides corresponding to a codon having been inserted into an otherwise wild-type sequence. Synthesis continues. At each site where an amino acid is to be inserted, another sub-stoichiometric coupling is carried out with either a unique trinucleotide (to generate one type of inserted amino acid) or a mixture of trinucleotide phosphoramidites (when up to 19 different residues are to be inserted at a single site).

(ii) Substitution (see FIG. 2)

In a third embodiment to generate substitution mutations during sub-stoichiometric coupling, the trinucleotide is chosen to have a stable 5' protecting group X (as defined above), and a differential deprotection scheme is applied. Following trinucleotide incorporation, during the next three monomer additions the 5' protecting group on the trinucleotide is not removed by the acid treatment that cleaves the 5'-DMT group of the coupled monomers. Consequently, the small fraction of growing chains that undergo an addition of the trinucleotide are not elongated. After the addition of three conventionally protected monomers to all other chains, which correspond in sequence to the wild-type codon, an additional step is carried out to remove the protecting group X at the end of the trinucleotide. Synthesis continues. At each codon where amino acid substitutions are to be generated, another coupling is carried out with either a unique trinucleotide (to generate one type of substituted amino acid) or a mixture of trinucleotide phosphoramidites (when up to 19 different residues are to be introduced at a single site).

(iii) Deletion (see FIG. 3)

In a fourth embodiment, deletions can be made by using a mononucleotide with a stable 5' protecting group X. The stable 5'-protecting group X (as defined above) delineates one boundary of the deletion and prevents subsequent coupling to the small percentage of chains which acquire it. Subsequent stoichiometric coupling of normal monomers occurs only to those chains which are deprotected during the course of the synthesis. Removal of the stable protecting group allows subsequent coupling to all chains and defines the second boundary of the deletion. This process can be repeated many times during one round of oligonucleotide synthesis, producing populations of oligonucleotides with many different deletions.

(iv) Substitution and Insertion

In a fifth embodiment, both substitutions and insertions can be made during a single synthesis. In this case, both 5'-X and 5'-DMT trinucleotides are used during a single oligonucleotide synthesis. Following incorporation of the differently protected trinucleotides, the 5'-DMT trinucleotide is deprotected and therefore undergoes subsequent extension, while the 5'-X trinucleotide remains protected and is not elongated. Cleavage of the 5'-X group from those chains which acquired it allows its subsequent extension. In this way both substitutions and insertions can be generated in a single synthesis.

The mixed sequences generated using trinucleotides for DNA synthesis can be used in standard oligonucleotide mutagenesis reactions to produce a very complex mixture of mutant genes. Genetic selection, genetic screening and nucleotide sequencing of the mutant genes will identify individual mutations, and appropriate expression systems will allow for the production of the corresponding mutant oligo- or polypeptides or proteins.

Trinucleotides (as opposed to oligonucleotides that are not multiples of 3 in length) offer the advantage that they are only coupled onto the oligonucleotide at positions that correspond to codon boundaries. Therefore, all sequence changes will be in the correct reading frame. Another advantage is that both substituting and inserting trinucleotides can be used in the same synthesis, permitting the generation of extremely complex mixtures of oligonucleotides capable of encoding many millions of mutant forms of the protein undergoing mutagenesis. Although coupling trinucleotides in the wild-type sequence is useful in protein mutagenesis, the present method can also be used to couple oligonucleotides of various lengths. This is an advantage over prior art techniques where only monomer substitutions were possible.

In its most generalized form, the invention involves coupling modified, activated oligonucleotides to produce sequence degeneracy. The added oligonucleotide may be of any length, although trinucleotides are of particular interest in protein mutagenesis. For generation of insertion mutations, a conventional 5'-DMT protecting group may be used. For generation of substitution or deletion mutations a stable 5' protecting group is used with a differential or orthogonal deprotection scheme.

A first object of this invention is to generate a mixture of oligonucleotides in a single automated synthesis.

A second object of this invention is to generate one or more amino acid substitutions in a wild-type sequence.

A third object of this invention is to generate one or more amino acid insertions in a wild-type sequence.

A fourth object of this invention is to generate one or more amino acid deletions in a wild-type sequence.

A fifth object of this invention is to generate a mixture of amino acid substitutions, deletions and insertions in a wild-type sequence.

A sixth object of this invention is to produce enormous amino acid sequence variations in a wild-type sequence, such as in the vitro randomization of the variable regions of cloned immunoglobulin genes to produce more efficient catalytic antibodies.

A seventh object of this invention is to add oligonucleotides (of various lengths) at selected sites in a gene sequence as substitutions and/or insertions and/or deletions.

DETAILED DESCRIPTION OF THE PREFERRED EMBODIMENTS

The present invention provides an efficient method for synthesizing oligonucleotides of mixed sequence, and also for generating insertions, deletions and substitutions in genes of wild-type sequence. The invention permits the use of conventional solid-phase synthesizers to produce a mixture of oligonucleotides in a single automated synthesis. The invention permits the insertion and/or substitution of small sequences, generally trinucleotides, across a defined segment of a cloned gene. When a trinucleotide (or a small oligonucleotide having a nucleotide length with a multiple of 3) is used, in-phase codon insertions or substitutions are achieved in the correct reading frame.

The first embodiment of the present invention is the stoichiometric coupling of one or more trinucleotides during automated DNA synthesis. Typically, synthesis is carried out using a commercially available automated synthesizer. The normal synthesis programme is used until it is necessary to couple the trinucleotide. At this point, the programme is suspended and the synthesizer is instructed to access a bottle fitted at an additional port containing a prepared solution of the trinucleotide. The trinucleotide bears protecting groups and an activated 3' position which are compatible with conventional chemical synthesis of DNA. For example, the 5' position of the trinucleotide can be protected as a DMT ether, and the 3' position activated as a phosphoramidite. Thereafter, synthesis continues in the usual way. On completion of the synthesis, the oligonucleotide is released from the column and the bases and phosphate esters deprotected. If the bases are protected with the conventional benzoyl and isobutyroyl amides, and the phosphates as b-cyanoethyl esters, treatment with hot, concentrated ammonia can be used to bring about complete deprotection. If the phosphates are protected as methyl esters, an additional step must be included before the hot ammonia treatment, in which phosphate deprotection is brought about with, for example, thiophenol, using well-established conditions. In a preferred embodiment, mixed oligonucleotides can be prepared by using mixtures of trinucleotides instead of a single trinucleotide during the synthesis protocol. Synthesis of oligonucleotides of mixed composition is achieved exactly as described above, except that a solution containing two or more trinucleotides is accessed when desired.

Figure 1:
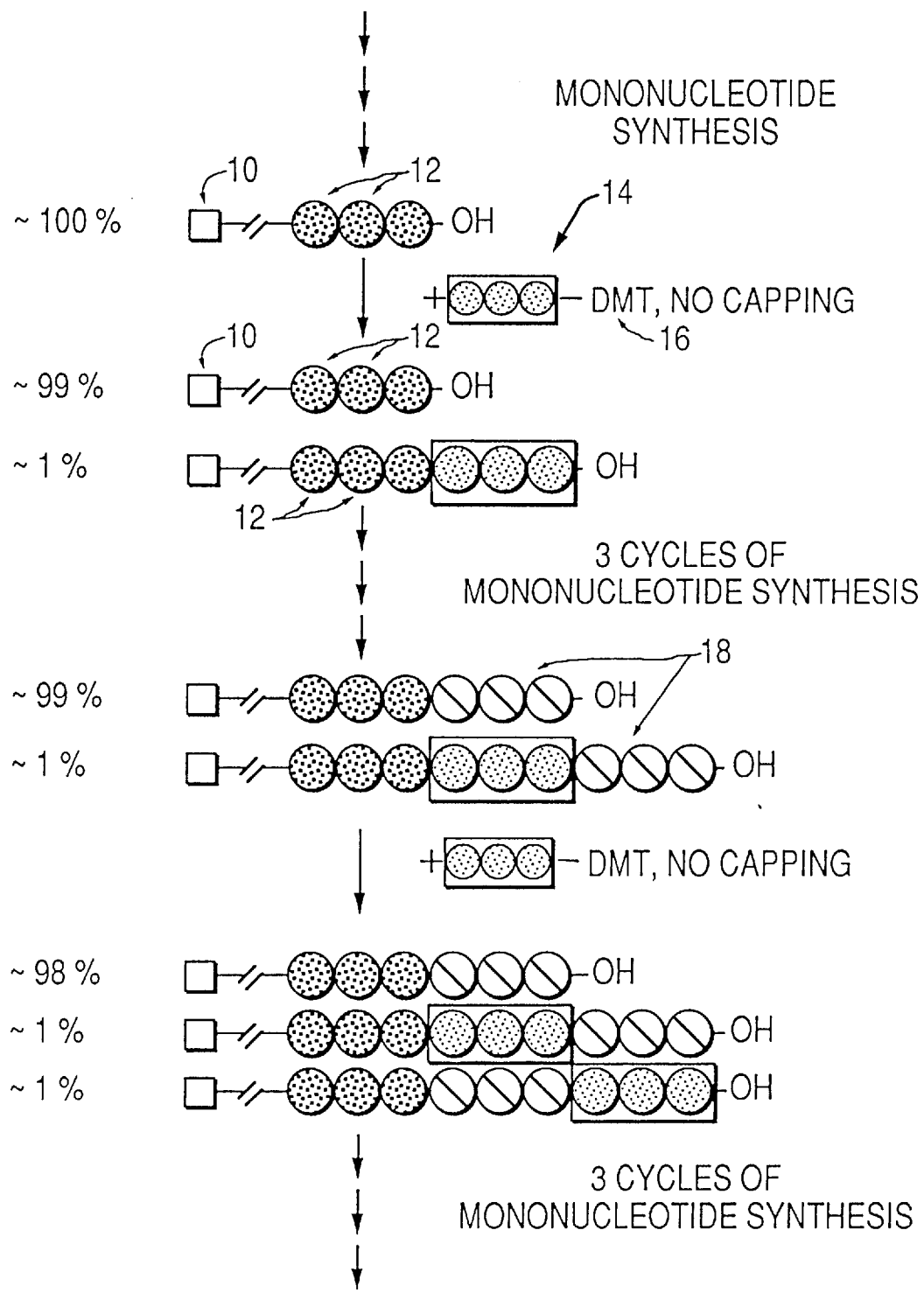
FIG. 1 is a schematic outline of the steps used to synthesize an oligonucleotide mixture containing single codon insertions during sub-stoichiometric coupling. The trinucleotide is shown by three filled circles surrounded by a rectangle. Monomeric building blocks used prior to trinucleotide coupling are filled circles. Those added after the trinucleotide are indicated by hatched circles.

The second embodiment of the present invention, shown in FIG. 1, is used to insert trinucleotides into a wild-type sequence during sub-stoichiometric coupling. This embodiment is valuable in producing in-phase codon insertions which may be used to generate proteins with modified structures and functional activities. As shown in FIG. 1, oligonucleotide synthesis is initiated from a nucleotide attached to a solid-phase support and continues from left to right by the coupling of mononucleotides. When synthesis reaches a position in the wild-type sequence where an insertion is to be made (i.e. at a codon boundary), a trinucleotide corresponding to a specific codon is coupled to a small percentage (~1%) of all growing oligonucleotide chains. The DMT protecting group on the 5' end of the trinucleotide is then removed, and three more mononucleotides are added to all of the oligonucleotide chains. At this point, the synthesis has advanced to the next codon boundary in the wild-type sequence, and the cycle of (i) sub-stoichiometric coupling of the trinucleotide followed by (ii) removal of the DMT protecting group is repeated, thereby inserting a trinucleotide at the next target site in the chain. In effect, the wild-type "background" sequence is synthesized with mononucleotide coupling, whereas all couplings involving a trinucleotide yield an insertion mutant.

Thus by superimposing sub-stoichiometric couplings of the trinucleotide mixture at positions of codon boundaries on an otherwise conventional automated synthesis of a wild-type oligonucleotide of length n, a heterogeneous mixture of oligonucleotides is generated. The exact composition of this mixture will depend on the number of trinucleotide couplings and their coupling efficiency. Whatever its composition, urea-polyacrylamide gel electrophoresis can be used to fractionate the mixture on the basis of length, permitting the n+3 band encoding all single codon insertions to be separated from the wild-type band and other bands encoding multiple insertions. If desired, oligonucleotides encoding multiple insertions can also be separated on urea-polyacrylamide gels.

Figure 2:
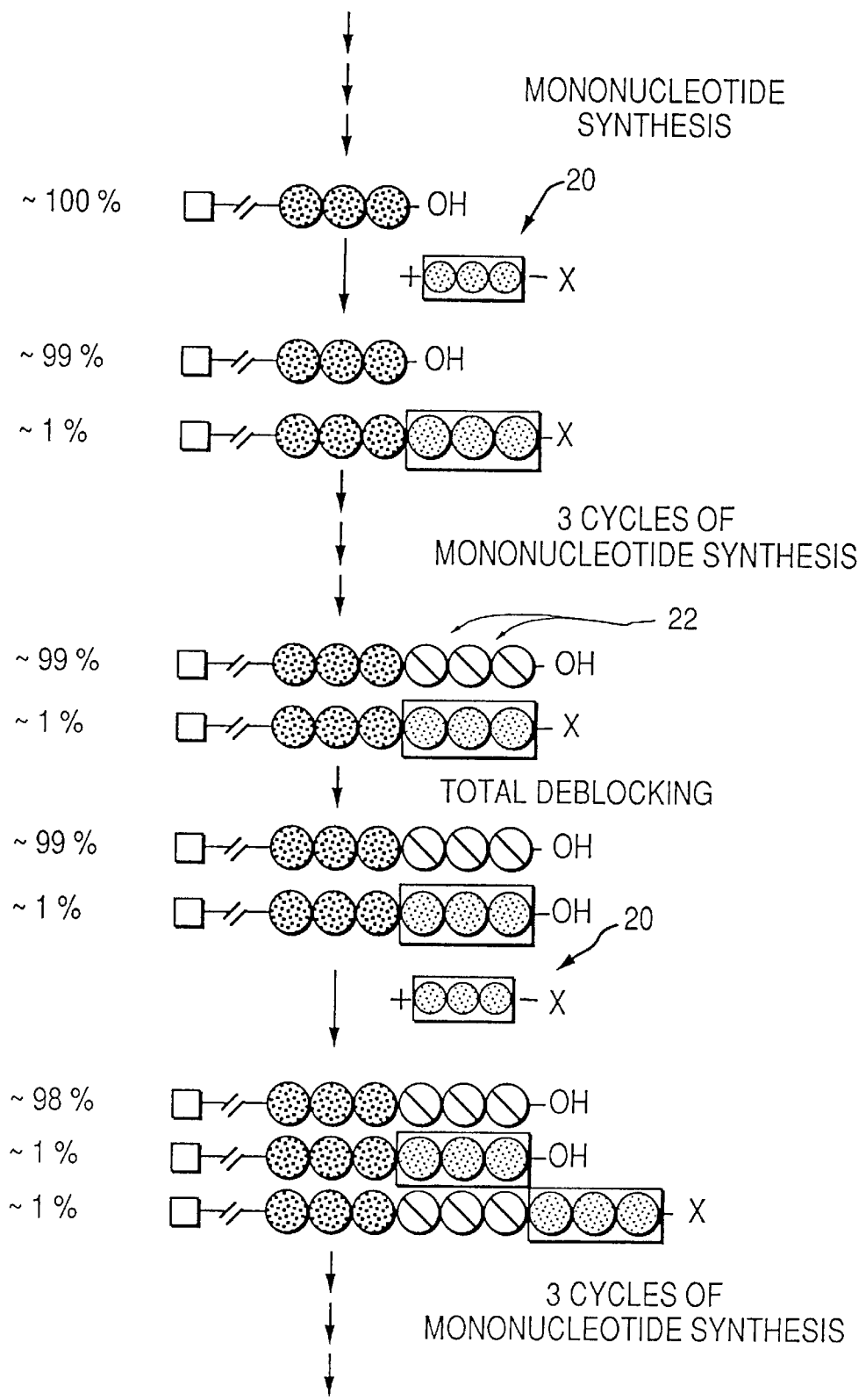
FIG. 2 is a schematic outline of the steps used to synthesize an oligonucleotide mixture containing single codon substitutions during sub-stoichiometric coupling. The trinucleotide and monomeric building blocks are as defined for FIG. 1. X is a particularly stable protecting group as defined in the text.

A third embodiment of the present invention is the sub-stoichiometric coupling of trinucleotides for generation of substitution mutations. Although this embodiment may also work well for the substitution of a small oligonucleotide of any length, a trinucleotide is discussed because of its usefulness in protein mutagenesis. As outlined in FIG. 2, the only modification required is the replacement of the 5'-DMT protecting group on the trinucleotide with a protecting group 5'-X that is stable to weak acid and the other conditions used in DNA synthesis, but labile to other mild deprotection conditions. (Various protecting groups can be used, the following is a partial list: (i) levulinate (see van Boom, J. H. & Burgers, P. M. J. (1976) *Tetrahedron Lett.* 4875–4878), (ii) silyl ether (see Ogilvie, K. K., Schifman, A. L., & Penny, C. (1979) *Can J. Chem.* 57, 2230–2238), (iii) fluoren-9-ylmethoxycarbonyl (Fmoc) (see Xu, Y., Lehmann, C., Slim, G., Christodoulou, C., Tan, Z., & Gait, M. J. (1989) *Nucl. Acids Res. Symp. Ser.* 21, 39–40), (iv) tert-butyldimethylsilyl, (v) allyloxycarbonyl, (vi) dibromomethylbenzoyl, (vii) 5'-O-b-substituted ethylsulfonyl, (viii) tetrahydropyranyl (Thp), (ix) methoxytetrahydropyranyl (Mthp), (x) 1-[(2-chloro-4-methyl)

phenyl]4-methoxypiperidin-4-yl (Ctmp), (xi) trityloxyacetyl and (xii) tetraisopropyldisiloxy). After coupling of an X-blocked trinucleotide to 1–3% of chains, the subsequent three monomer couplings add the next wild-type codon to the 97–99% of chains that did not acquire the trinucleotide, but not to those chains that coupled to the trinucleotide. At this point in the synthesis, deprotection of all chains (mild-acid to release DMT; dilute aqueous hydrazide if X is levulinate; fluoride if X is a silyl ether; dilute base if X is Fmoc) would yield 1–3% of chains with a substitution of the codon specified by the trinucleotide and 97–99% of chains that are still wild-type in sequence. As with the insertion-generating strategy, repetition of the basic cycle of 1 sub-stoichiometric trinucleotide coupling followed by 3 stoichiometric monomer couplings can be used to introduce mutations at each position across the gene segment defined by the oligonucleotide sequence. Although purifying mutagenic oligonucleotides away from those with the wild-type sequence on the basis of size is not feasible, it is possible to use trinucleotide blocks containing one or two phosphonate or thiophosphate linkages, permitting purification on the basis of charge or chromatographic properties.

Figure 3:
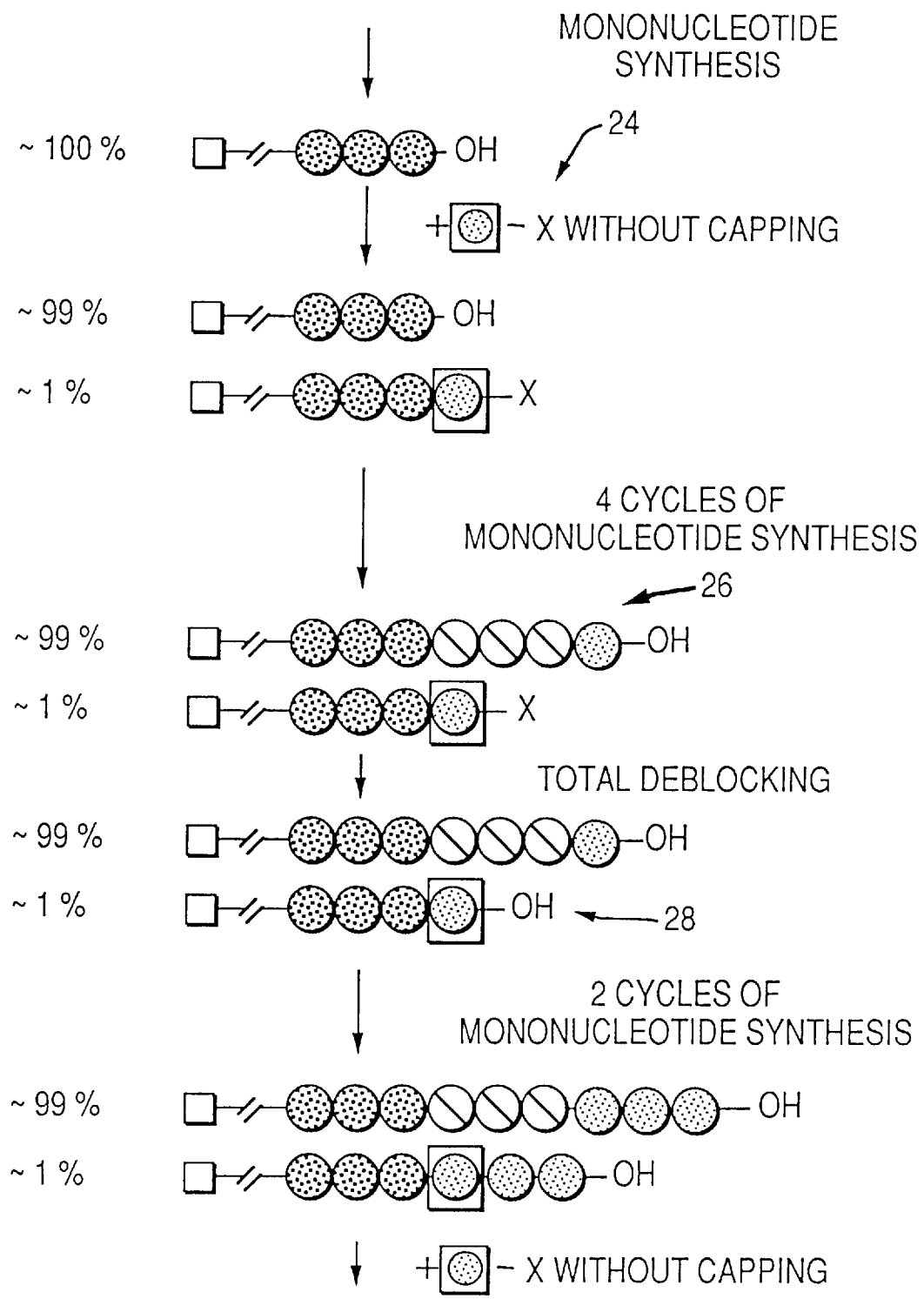
FIG. 3 is a schematic outline of the steps used to synthesize an oligonucleotide mixture containing single codon deletions during sub-stoichiometric coupling. The grey circle surrounded by a square is the X-protected mononucleotide building block, where X is a particularly stable protecting group as defined in the text. Filled circles are conventional monomeric building blocks coupled prior to addition of the X-monomer, hatched circles are the three monomeric building blocks coupled following addition of the X-monomer which define a codon. Grey circles are monomeric building blocks coupled following deprotection of the X-monomer.

A fourth embodiment of the present invention is the use of differentially protected monomers for deletion mutagenesis. As shown in FIG. 3, codon deletions can be generated through the use of X-protected mononucleotides by sub-stoichiometric couplings followed by four DMT-monomer addition cycles prior to total deprotection. Again, synthesis proceeds normally until the boundary of a codon which is to be deleted is reached. At the codon boundary, a sub-stoichiometric amount of a 5'-X-mononucleotide phosphoramidite capable of preserving the wild-type amino acid sequence of the adjacent codon is coupled. Four cycles of conventional, stoichiometric, mononucleotide coupling to all of the chains which did not receive the differentially protected mononucleotide serve to add the codon which will eventually be deleted, plus an additional mononucleotide. At this point, the 5'-X protecting group is removed and two more rounds of conventional mononucleotide coupling finish the synthesis of the codon bordering the deletion site. The whole cycle can then be repeated. Eventually, a large population of oligonucleotides encoding single codon deletions will be produced which can then be used to direct mutations as described previously.

These general schemes can be useful in cases where enormous sequence variation is desired, such as the in vitro randomization of the variable regions of cloned immunoglobulin genes to produce more efficient catalytic antibodies. Likewise, projects that seek to develop tight binding ligands via phage display libraries and peptide segment display on enzymes could make use of the enormous sequence complexity which can be generated using trinucleotides, especially in the later stages of optimization of an initial modestly tight binding sequence. For purposes of simplicity, the substitution embodiment and insertion embodiment described above taught a trinucleotide insertion or substitution. As discussed previously, use of a trinucleotide is of particular interest when performing an amino acid substitution or insertion. However, it is possible to introduce the sequence degeneracy with small oligonucleotides of any length.

The above disclosure generally describes the present invention. A more complete understanding can be obtained by reference to the following specific examples which are provided herein for purposes of illustration only and are not intended to limit the scope of the invention.

EXAMPLE 1

Synthesis of Trinucleotides[1]

A. Synthesis of 5'-DMT-dCBz-[PO(OMe)]-dT-[PO(OMe)]-dT-3'-[P(OMe)(NiPr2)].

To a solution of dT-3'-Fmoc (930 mg, 2.0 mmol), (prepared from the corresponding 5'-DMT derivative by trichloroacetic acid-catalysed detritylation) and 5'-DMT-dT-3'-[P(OMe)(NiPr2)] (1.5 g, 2.1 mmol) in anhydrous acetonitrile, was added tetrazole (150 mg, 2.1 mmol). After 30 minutes at room temperature, the phosphite was oxidised with t-butyl hydroperoxide (0.31 ml of an 80% solution in di-t-butyl hydroperoxide, 2.5 mmol), and excess tetrazolophosphoramidite was

[1] Abbreviations: Me=methyl, Bz=benzyl, $^i$Pr=iso-propyl. For the sake of convenience, trinucleotides are in some cases abbreviated as, for example, dTdTdT. quenched with methanol. The solution was evaporated, and the DMT group cleaved by treatment with a solution of trichloroacetic acid (0.82 g, 5.0 mmol) in dichloromethane. The DMT cation was quenched with 10 mM sodium bicarbonate solution, and the 5'-HO-dT-[PO(OMe)]-dT-3'-Fmoc was extracted with dichloromethane. The organic layer was dried (Na2SO4), filtered, and evaporated, and the residue purified by silica gel chromatography using a 0–8% gradient of methanol in dichloromethane (Rf=0.30 in 10% methanol/dichloromethane), yielding 1.1 g (70%) of 5'-HO-dT-3'-[PO(OMe)]-dT-3'-Fmoc.

To a solution of purified 5'-HO-dT-3'-[PO(OMe)]-dT-3'-Fmoc (780 mg, 1.0 mmol) and 5'-DMT-dCBz-3'-[P(OMe)(NiPr2)] (950 mg, 1.2 mmol) in anhydrous acetonitrile, was added tetrazole (83 mg, 1.2 mmol). After 30 minutes at room temperature, the phosphite was oxidised with t-butyl hydroperoxide (0.19 ml of an 80% solution in di-t-butyl hydroperoxide, 1.5 mmol), and excess tetrazolophosphoramidite was quenched with methanol. The solution was evaporated, and the residue purified by chromatography on basic alumina using a 0–8% gradient of methanol in dichloromethane (Rf=0.42 in 10% methanol/dichloromethane), yielding 790 mg (53%) of 5'-DMT-dCBz-[PO(OMe)]-dT-[PO(OMe)]-dT-3'-Fmoc.

The purified, fully protected trinucleotide (300 mg, 0.2 mmol) in dichloromethane was treated with triethylamine (100 mg, 1.0 mmol) at room temperature for 90-minutes to remove the 3'-Fmoc group. The 3'-OH trinucleotide (Rf= 0.26 in 10% methanol/dichloromethane) was then treated with chloro-N,N-diisopropylaminomethoxyphosphine (40 mg, 0.3 mmol) at room temperature for 30 minutes. Excess chlorophosphine was quenched with methanol, the solution was washed with water, dried (MgSO4), and the trinucleotide phosphoramidite was recovered by precipitation from hexane, yielding 230 mg (80%) of 5'-DMT-dCBz-[PO(OMe)]-dT-[PO(OMe)]-dT-3'-[P(OMe)(NiPr2)].

B. Preparation of DNA using 5'-DMT-dCBz-[PO(OMe)]-dT[PO(OMe)]-dT-3 '-[P(OMe)(NiPr2)].

In all cases, automated DNA synthesis was carried out on either an Applied Biosystems ABI 340B or 380B Synthesizer. The phosphoramidite was dissolved in anhydrous acetonitrile to a concentration of 10 mM, and fitted to the fifth port of the synthesizer. Following coupling of three monomers to the column, the trinucleotide was delivered in a double coupling procedure,. The coupling yield was determined by measuring the release of DMT cation. A yield in excess of 95% was obtained. On completion of the synthesis, the heptanucleotide was released from the solid support and the bases deprotected by treatment with concentrated aqueous ammonia in the usual way. Polyacrylamide gel electrophoresis (20%) and HPLC (C18 column, 0.1M triethylammonium acetate/acetonitrile) confirmed the formation of heptanucleotide and the absence of any failure sequences.

EXAMPLE 2

Insertion Mutagenesis

A. General Procedure for Insertion of a Single Trinucleotide into the Gene for Staphylococcal Nuclease.

Synthesis used the standard 0.2 mmol synthesis routine, modified to eliminate the capping step after sub-stoichiometric addition of the trinucleotide. Trinucleotide phosphoramidite (25 mg) was dissolved in anhydrous acetonitrile and the vial attached to the fifth injection port of the synthesizer. Coupling efficiencies of individual monomer and trinucleotide additions were monitored by the release of the 5'-DMT group. The concentration of the unpurified oligonucleotide was estimated from the absorbance at 260 nm.

After synthesis, 10–15 nmol of impure oligonucleotide was phenol extracted, vacuum dried, and re-suspended in 5≠1 of 5 mM NaCl, 1 mM EDTA, 10 mM Tris.HCl, pH 8.1 at 65iC for 30 minutes. An equal volume of 95% formamide, 20 mM EDTA, 0.1% bromophenol blue, and 0.1% xylene cyanol was added, the samples heated at 100iC for 2 minutes, loaded onto a 0.4 mm thick by 42 cm long 15–20% polyacrylamide gel, and electrophoresed at 750 V until the xylene cyanol was half-way down the gel. The gel was stained in 2 mg/ml ethidium bromide for 30 minutes, oligonucleotide bands were visualized by UV illumination, and a 0.5–1.0 cm section of gel immediately above the major band was excised and eluted overnight in 300 mM sodium acetate, 5 mM EDTA at 37iC. After brief centrifugation to remove particulates, the oligonucleotide mixture was ethanol precipitated.

The impure oligonucleotide mixture was radiolabelled with [g-32P]ATP using polynucleotide kinase, in order to confirm the presence of the n+3 band and to quantitate its recovery. Approximately 1 pmol of purified n+3 oligonucleotide was used to mutagenize a uracil-containing M13 derivative phage carrying the gene for staphylococcal nuclease. Mutant plaques were identified using a chromogenic indicator agar, and the nuclease gene of each mutant phage was sequenced in its entirety by the dideoxy method.

B. General Technique for Insertion of One or Two Codons.

A sub-stoichiometric coupling of a mixture of DMT-dGdCdT-phosphoramidite and DMT-dGdGdT-phosphoramidite was carried out during synthesis of mutagenic oligonucleotides for the staphylococcal nuclease gene. Following this reaction, which yielded 1–3% coupling, the standard capping step with acetic anhydride was omitted. (Otherwise, the 97–99% of chains that did not undergo reaction would have been inactivated to additional couplings.) The subsequent steps of phosphite oxidation and deprotection of the 5'-DMT group were carried out exactly as in conventional monomer addition cycles. At this point in the synthesis, 1–3% of chains had an additional dGdCdT or dGdGdT codon at their 5'ends, whereas the remaining 97–99% were wild-type in sequence. Next, three monomer addition cycles were carried out so that both the normal length chains and the chains with an extra codon received the next wild-type codon. Again, a codon boundary had been reached; in order to induce single codon insertions at this position, another round of sub-stoichiometric coupling of the trinucleotide mixture was carried out with omission of the 5' capping reaction. At this point in the synthesis, 1–3.% of chains had acquired the second insertion of either dGdCdT or dGdGdT, 1–3% had acquired the first, less than 0.1% had both insertions, and the remaining majority had the sequence of wild-type. Three more monomer addition cycles were then carried out to attach the next wild-type codon to all chains. Further couplings of the trinucleotide mixture were carried out after every third monomer coupling until codons had been inserted at all targeted sites. A final 6–9 monomer couplings then followed to increase the amount of wild type sequence homology needed for priming second strand synthesis on a single-stranded DNA template by the oligonucleotide.

C. Use Of dGdCdT Trinucleotide for Single Codon Insertion Mutagenesis.

Insertions of the trinucleotide dGdCdT were made at the codon boundaries 64/65, 65/66, and 66/67 of the staphylococcal nuclease gene. When the purified oligonucleotide mixture was used to mutagenize single-stranded phage, 15% of the resulting phage plaques were deficient in nuclease activity. Of the 24 mutant isolates that were sequenced, 11 had a dGdCdT insertion at 65/66, 11 a dGdCdT insertion at 66/67, one was wild-type, and one had a single nucleotide deletion within the oligonucleotide sequence, presumably due to contaminating n−1 oligonucleotide not removed by the gel electrophoresis purification step. An identical experiment that targeted dGdGdT insertions to these same three sites gave five dGdGdT insertions at 64/65, ten at 65/66, three at 66/67, one wild-type, one single nucleotide deletion, and four mutations due to the oligonucleotide mis-pairing at other sites in the nuclease gene.

D. Use of dGdCdT and dGdGdT Trinucleotides for Multiple Codon Insertion Mutagenesis.

Figure 4A:
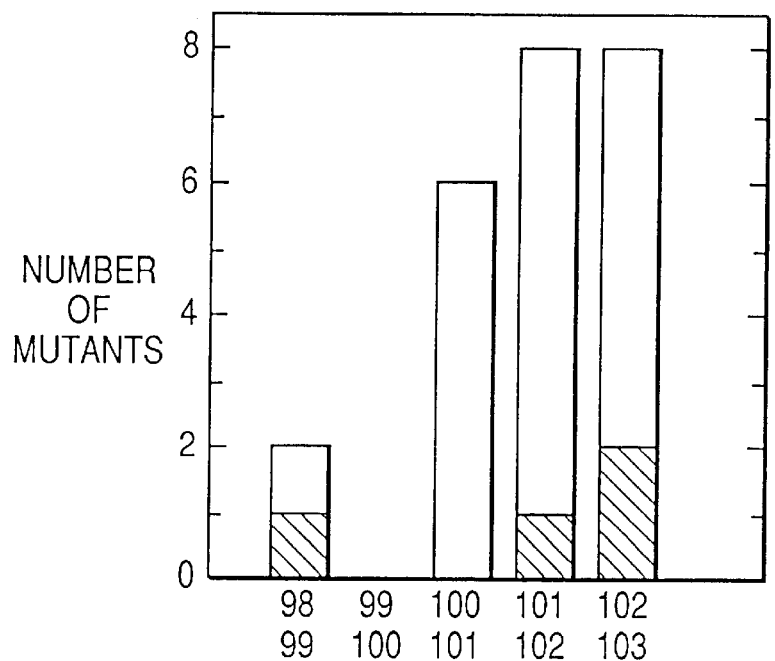
FIGS. 4A and 4B are histograms showing the distribution and frequencies of alanine and glycine codon-insertion mutations recovered in the gene for staphylococcal nuclease. Two experiments were performed, directing insertions to different parts of the gene (4A and 4B). The horizontal axis defines codon boundaries, the vertical axis, the numbers of mutants. Alanine mutants are shaded, and glycine mutants are the open portion of the bars.
Figure 4B:
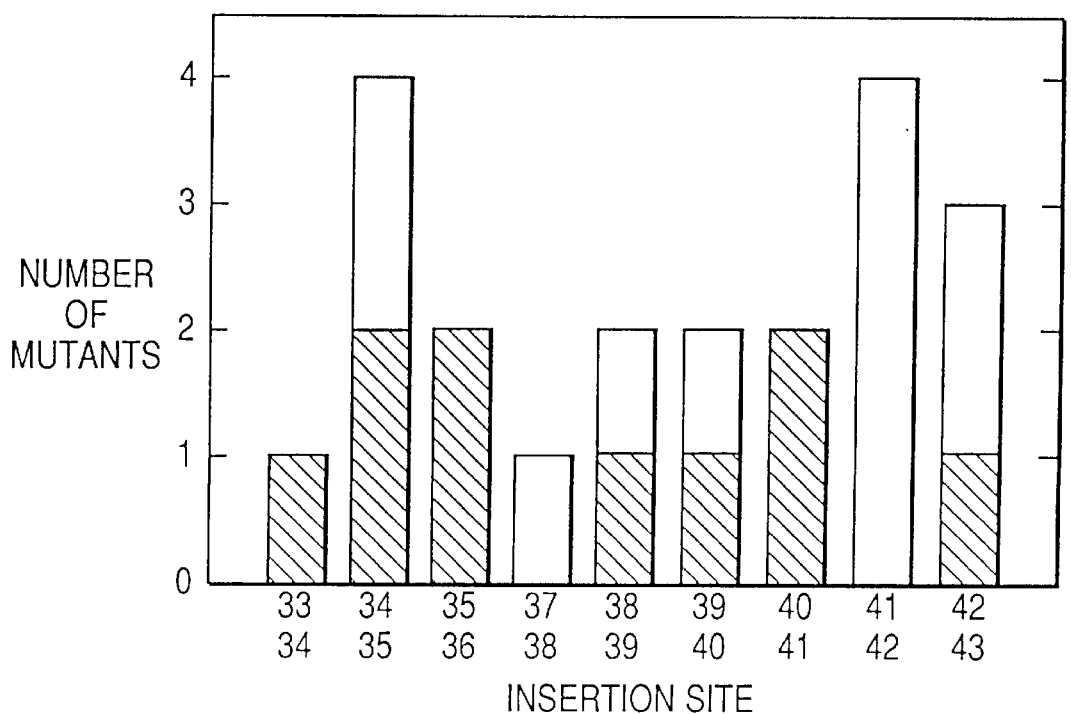

FIGS. 4A and 4B show the results of two experiments in which equimolar mixtures (4.1 mM) of 5'-DMT-dGdCdT-phosphoramidite and 5'-DMT-dGdGdT-phosphoramidite were used for insertion mutagenesis. The histogram shows the distribution and frequencies of alanine (shown in the shaded portion of the bar graph) and glycine (shown in the open portion of the bar graph) codon-insertion mutations recovered in the gene for staphylococcal nuclease. In the first experiment, an oligonucleotide of wild-type length n=29 was made, with insertions targeted to each of the 5 codon boundaries between codons 98 and 103 of the staphylococcal nuclease gene. Twenty-four of the 38 mutant plaques contained single codon insertions, with all sites represented except 99/100 (FIG. 4A). Thirteen of the remaining mutants displayed a single nucleotide deletion within the oligonucleotide sequence consistent with mutagenesis by an oligonucleotide from the contaminating n−1 band. In addition, one single nucleotide insertion was found.

In the second experiment, an oligonucleotide of wild-type length n=46. was synthesized to direct insertions to nine of the ten codon boundaries between codons 33 and 43 of the staphylococcal nuclease gene. In this case 21 of the 37 mutant plaques sequenced contained a single dGdGdT or dGdCdT insertion at a targeted site; the distribution of these insertions is shown in FIG. 4B. Again, single nucleotide deletions within the oligonucleotide were the major contaminant (twelve isolates), with two single nucleotide insertions plus two larger deletions making up the remainder.

EXAMPLE 3

Substitution Mutagenesis

A. Synthesis of Trinucleotide Phosphoramidite Coding for Leucine with a Fmoc (fluoren-9-ylmethoxycarbonyl) Protecting Group.

A trinucleotide specifying a leucine codon can be custom synthesized using standard solution phase chemistry.

Re-suspension of the 5'-OH trinucleotide in dry pyridine followed by incubation with 1.5 equivalents of Fmoc-Cl at 0iC for one hour can produce the 5'-Fmoc protected trinucleotide in greater than 50% yield. RP-HPLC can be used to purify the 5'-Fmoc trinucleotide and its structure can be supported using 1H-NMR spectroscopy (Lehmann, C., Xu, Y., Christodoulou, C., Tan, Z. and Gait, M. J. (1989) *Nucl. Acids Res.* 17, 2379–2389). Standard methods (see, Balgobin, N. and Chattopadhyaya, J. (1987) *Nucleosides and Nucleotides* 6, 461–463) can be used to phosphitylate the 5'-Fmoc trinucleotide and purify the resulting phosphoramidite. The structure of the final product, 5'-Fmoc-dCBz-[PO(OMe)]-dT-[PO(OMe)]-dT-3'-[P(OMe)(NiPr2)] can be supported using 1H and 31P-NMR spectroscopy and can be confirmed by DNA sequencing of the mutations induced by the trinucleotide. The lyophilized product should be stored in 25 mg portions under argon in amber vials at −70° C.

B. Codon Substitution with the 5'-O-Fmoc-dCdTdT Phosphoramidite.

Oligonucleotides can be synthesized on a 340B Applied Biosystems DNA synthesizer using the commercially provided 0.2≠mol synthesis routine. The routine is modified to eliminate the capping step after the sub-stoichiometric addition of the trinucleotide. A step is added in which 100 mM DBU (1,8-diazabicyco-[5.4.0]-undec-7-ene) is added from a separate vial to effect removal of the 5'-Fmoc protecting group of the coupled trinucleotide after three subsequent mononucleotide coupling cycles. Mononucleotide and trinucleotide coupling efficiencies can be measured by monitoring the absorbance of the released DMT and Fmoc groups at 498 and 305 nm respectively. The final oligonucleotide product containing a 5'-DMT group can be cleaved from the solid support and purified away from truncated product by RP-HPLC before standard removal of the remaining protecting groups.

Oligonucleotide concentration can be estimated from the absorbance at 260 nm. Approximately 1 pmol of purified oligonucleotide can be used to mutagenize a uracil-containing M13 phage (see Kunkel, T. A. (1985) *Proc. Natl. Acad. Sci. USA* 82, 488–492) carrying the gene for staphylococcal nuclease. Mutant plaques can be identified by using a chromogenic indicator agar (see Shortle, D. (1983) *Gene* 22, 181–189), and the nuclease gene of each mutant phage can be sequenced in its entirety by the dideoxynucleotide chain termination method (see Sanger, F., Nicklen, S. and Coulson, A. R. (1977) *Proc. Natl. Acad. Sci. USA* 74, 5463–5467).

EXAMPLE 4

Deletion Mutagenesis

A. Synthesis of a Deoxythymidine Mononucleotide Phosphoramidite with a 5'-Fmoc (fluoren-9-ylmethoxycarbonyl) Protecting Group.

Suspension of deoxythymidine in dry pyridine followed by incubation with 1.5 equivalents of Fmoc-Cl at 0iC for one hour can produce the 5'-Fmoc protected mononucleotide in greater than 50% yield. RP-HPLC can be used to purify the 5'-Fmoc mononucleotide and its structure can be supported using 1H-NMR spectroscopy (Lehmann, C., Xu, Y., Christodoulou, C., Tan, Z. and Gait, M. J. (1989) *Nucleic Acids Res.* 17, 2379–2389). Standard methods (see, Balgobin, N. and Chattopadhyaya, J. (1987) *Nucleosides and Nucleotides* 6, 461–463) can be used to phosphitylate the 5'-Fmoc mononucleoside and purify the resulting 3'-phosphoramidite. The structure of the final product, 5'-FmocO-dT-3'-[P(OMe)(NiPr2)] can be supported using 1H and 31P-NMR spectroscopy and can be confirmed by DNA sequencing of the mutations induced using the mononucleotide. The lyophilized product should be stored in 25 mg portions under argon in amber vials at −70iC.

B. Oligonucleotide Synthesis with Codon Deletion.

Oligonucleotides can be synthesized on a 340B Applied Biosystems DNA synthesizer using the commercially supplied 0.2 μmol synthesis routine. The routine is modified to eliminate the capping step after sub-stoichiometric addition of the mononucleotide. A step is included in which 100 mM DBU is added from a separate vial to effect removal of the 5'-Fmoc protecting group of the coupled trinucleotide after four subsequent mononucleotide coupling cycles. 5'-Fmoc mononucleotide and 5'-DMT-mononucleotide coupling efficiencies can be measured by monitoring the absorbance of the released DMT and Fmoc groups at 498 and 305 nm respectively. The final oligonucleotide product can be cleaved from the solid support and purified on the basis of size before standard removal of the remaining protecting groups.

Oligonucleotide concentration can be estimated from the absorbance at 260 nm. Approximately 1 pmol of purified oligonucleotide can be used to mutagenize a uracil-containing M13 phage as above. Mutant plaques can be identified by using a chromogenic indicator agar, and the nuclease gene of each mutant phage can be sequenced in its entirety by the dideoxynucleotide chain termination method as above.

The invention claimed is:

1. A method for introducing an insertion mutation at one or more selected positions during the chemical synthesis of a population of DNA molecules of known sequence, said method comprising the steps of:
   (a) sub-stoichiometric coupling of oligonucleotides to a population of DNA molecules or mononucleotides having a sequence consisting of a portion of the known sequence, said oligonucleotides bearing a 5'-protecting group that is cleaved under a set of conditions used to remove 5'-protecting groups of mononucleotides, wherein said oligonucleotides further comprise protected phosphates, protected bases, and a 3'-phosphoramidite group, wherein said coupling is performed without capping,
   (b) removing all 5'-protecting groups under said set of conditions,
   (c) continuing DNA synthesis by coupling mononucleotides to said population of DNA molecules or repeating steps (a) and (b) at a second selected position and continuing DNA synthesis by coupling of mononucleotides to said population of DNA molecules to form a population of DNA molecules consisting of the known sequence with one or more oligonucleotide insertion mutations.

2. The method of claim 1 wherein said oligonucleotides comprise acid-labile groups protecting free 5' positions, methyl or cyanoethyl ester groups protecting phosphates, benzoyl or isobutyryl amides protecting bases, and 3'-O-methyl or O-cyanoethyl N,N-diisopropylamino phosphoramidite groups.

3. A method for introducing a substitution mutation at one or more selected positions during the chemical synthesis of a population of DNA molecules of known sequence, said method comprising the steps of:
   (a) sub-stoichiometric coupling of oligonucleotides having a sequence not according to the known sequence, said oligonucleotides consisting of a number of nucleotides, to a population of DNA molecules or mononucleotides, said oligonucleotides bearing first 5'-protecting groups that are stable to a first set of conditions used to remove 5'-protecting groups of mononucleotides, but labile to a second set of conditions used to remove 5'-protecting groups of mononucleotides, wherein said oligonucleotides further comprise protected phosphates, protected bases, and a 3'-phosphoramidite group, wherein said coupling is performed without capping, (b) sequentially and stoichiometrically adding said number of nucleotides to those DNA molecules which did not acquire said oligonucleotides bearing first 5'-protecting groups, wherein the nucleotides are added according to the known sequence, wherein the nucleotides bear second 5'-protecting groups, wherein said second 5'-protecting groups are labile to said first set of conditions, and removing said second 5'-protecting groups under said first set of conditions after each step of adding, (c) removing said first 5'-protecting groups on those DNA molecules which acquired said oligonucleotides using said second set of conditions, and (d) either continuing to synthesize DNA according to said known sequence using mononucleotides, or, repeating steps (a) though (c) to generate additional substitution mutations, and continuing to synthesize DNA according to said known sequence using mononucleotides, to form a population of DNA molecules consisting of the know sequence with one or more substitution mutations.

4. The method of claim 3 wherein said oligonucleotides comprise acid-labile groups protecting free 5' positions, methyl or cyanoethyl ester groups protecting phosphates, benzoyl or isobutyryl amides protecting bases, and 3'-O-methyl or O-cyanoethyl N,N-diisopropylamino phosphoramidite groups.

5. The method of claim 3 wherein said population of DNA molecules of known sequence encode peptides or proteins.

6. The method of claim 5 wherein said number is three or a multiple thereof.

7. The method according to either of claims 1 or 3, wherein said oligonucleotides said population of DNA molecules of known sequence encode peptides or proteins, and said selected positions are codon boundaries.

8. The method according to claim 7 wherein said oligonucleotides bear a 5'-DMT group.

9. The method according to claim 8 wherein said oligonucleotides comprises a multiplicity of species.

10. A method for introducing a deletion mutation at one or more selected positions during the chemical synthesis of a population of DNA molecules having a known sequence, said method comprising the steps of:

(a) sub-stoichiometric coupling of first mononucleotides to a population of DNA molecules having a sequence consisting of a portion of the known sequence of second mononucleotides, said first mononucleotides bearing a first 5'-protecting group that is stable under a first set of conditions used to remove 5'-protecting groups of mononucleotides, but which is labile to a second set of conditions used to remove 5'-protecting groups of mononucleotides, wherein said first mononucleotides comprise protected phosphates, protected bases, and a 3'-phosphoramidite group, wherein said coupling is performed without capping, (b) sequentially and stoichiometrically adding as least third and fourth mononucleotides bearing second 5'-protecting groups to those DNA molecules which did not acquire said first mononucleotides bearing said first 5'-protecting group, wherein said third and fourth mononucleotides correspond in sequence to the known sequence, wherein said second 5'-protecting groups are labile to a said first set of conditions, wherein said third or fourth mononucleotides bearing a second 5'-protecting group bears the same nucleotides moiety as said first mononucleotides, and removing said second 5'protecting groups under said first set of conditions after each step of adding, (c) removing the first 5'-protecting group from those DNA molecules which acquired the first mononucleotides bearing a first 5'-protecting group under said second set of conditions, and (d) either continuing to synthesize DNA according to said known sequence using mononucleotides, or, repeating steps (a) through (c) to generate additional deletion mutations in said DNA molecules of said population, and continuing to synthesis DNA according to said known sequence using mononucleotides, to form a population of DNA molecules having deletion mutations at one or more selected positions.

11. The method of claim 10 wherein said population of DNA molecules of known sequence encode peptides or proteins, and wherein said mononucleotides bearing a first 5'-protecting group are added at a codon boundary, and wherein said mononucleotides added in step consist of one or more codons.

12. The method of claim 10, wherein said mononucleotides comprise acid-labile groups protecting free 5' positions, methyl or cyanoethyl ester groups protecting phosphates, benzoyl or isobutyryl amides protecting bases, and 3'-O-methyl or O-cyanoethyl N,N-diisopropylamino phosphoramidite groups.

13. The method of claim 10 wherein said first mononucleotides conform to the known sequence and the fourth mononucleotides have the same nucleotide moiety as said first mononucleotides.

14. The method of claim 10 wherein said population of DNA molecules of known sequence encode peptides or proteins.

15. A method for introducing insertion and substitution mutations at one or more selected positions during the chemical synthesis of a population of DNA molecules of known sequence, said method comprising the steps of:

(a) coupling of a mixture of first oligonucleotides and second oligonucleotides consisting of a number of nucleotides to a population of DNA molecules or mononucleotides having a sequence consisting of a portion of the known sequence, said first oligonucleotides bearing a first 5'-protecting group that is labile under a first set of conditions used to remove 5'-protecting groups of mononucleotides, said second oligonucleotides bearing a second 5'-protecting group that is stable under said first set of conditions, but labile under a second set of conditions used to remove 5'-protecting groups of mononucleotides, wherein said first and second oligonucleotides further comprise protected phosphates, protected bases, and 5'-phosphoramidite groups, (b) removing said first 5'-protecting groups under said first set of conditions;

(c) continuing DNA synthesis by coupling said number of nucleotides according to said known sequence to said population of DNA molecules which did not acquire said second oligonucleotides, wherein the nucleotides bear 5'-protecting groups that are labile under the first set of conditions;

(d) removing said second 5'-protecting groups under said second set of conditions;

(e) continuing DNA synthesis by adding mononucleotides to said population of DNA molecules according to the known sequence of repeating steps (a) through (d) at a second selected position and continuing DNA synthesis by coupling of mononucleotides to said population of DNA molecules according to the known sequence to form a population of DNA molecules consisting of the known sequence with insertion of substitution mutations.

16. A method of preparing a population of DNA molecules of mixed sequences, which differ from each other at one or more positions within the DNA molecules, said method comprising the step of:

employing a mixed population of trinucleotides, said population comprising a selected combination of trinucleotides, for stoichiometric, essentially quantitative incorporation at one or more positions in a population of DNA molecules of mixed sequences, whereby the population of DNA molecules formed has a composition defined by the selected combination of trinucleotides, wherein each of said trinucleotides comprises a 3'-phosphoramidite group.

17. The method according to claim 16 wherein said populating of DNA molecules encode peptides or proteins and said trinucleotides are incorporated at one or more codon boundaries.

* * * * *

UNITED STATES PATENT AND TRADEMARK OFFICE
CERTIFICATE OF CORRECTION

PATENT NO.   : 5,869,644
DATED        : February 9, 1999
INVENTOR(S)  : David R. Shortle et al.

It is certified that error appears in the above-identified patent and that said Letters Patent is hereby corrected as shown below:

Column 18,
Lines 6-7, please correct "DNA molecules of mixed sequences" to -- DNA molecules being synthesized, to form a population of DNA molecules of mixed sequences --
Line 13, please correct "populating" to -- population --

Signed and Sealed this

Twelfth Day of October, 2004

JON W. DUDAS
*Director of the United States Patent and Trademark Office*